United States Patent [19]

Cleary et al.

[11] Patent Number: 5,062,793
[45] Date of Patent: Nov. 5, 1991

[54] DEBONDING INSTRUMENT FOR ORTHODONTIC BRACKETS

[75] Inventors: James D. Cleary; Robert P. Eckert, both of St. Paul, Minn.

[73] Assignee: Minnesota Mining and Manufacturing Company, St. Paul, Minn.

[21] Appl. No.: 404,954

[22] Filed: Sep. 8, 1989

[51] Int. Cl.⁵ ............................................... A61C 3/00
[52] U.S. Cl. .......................................................... 433/3
[58] Field of Search .................................. 433/3, 4, 159

[56] References Cited

U.S. PATENT DOCUMENTS

| | | | |
|---|---|---|---|
| 442,107 | 12/1890 | Davison . | |
| 3,507,043 | 4/1970 | Rubin | 32/63 |
| 3,755,902 | 9/1973 | Northcutt | 32/66 |
| 3,986,265 | 10/1976 | Cusato | 32/66 |
| 4,155,164 | 5/1979 | White | 433/3 |
| 4,248,587 | 2/1981 | Kurz | 433/4 |
| 4,553,932 | 11/1985 | Armstrong et al. | 433/4 |
| 4,569,979 | 6/1987 | Snead | 433/4 |
| 4,631,028 | 12/1986 | Kurz | 433/4 |
| 4,776,791 | 10/1988 | Hannula et al. | 433/4 |
| 4,850,864 | 7/1989 | Diamond | 433/3 |

FOREIGN PATENT DOCUMENTS

| | | | |
|---|---|---|---|
| 2236819 | 2/1973 | Fed. Rep. of Germany | 433/3 |
| 3534837 | 4/1987 | Fed. Rep. of Germany | 433/3 |

Primary Examiner—Robert P. Swiatek
Assistant Examiner—Nicholas D. Lucchesi
Attorney, Agent, or Firm—Gary L. Griswold; Walter N. Kirn; James D. Christoff

[57] ABSTRACT

An instrument for debonding orthodontic brackets from teeth has a pair of arms with pulling sections adapted to engage the bracket behind occlusal and gingival tie wings. The arms are connected to a lever, and movement of the lever enables the arms to simultaneously exert a pulling force on both of the wings along substantially their entire mesial-distal width in order to lift the bracket from the tooth in straight-line fashion. A pair of reaction supports for engagement with the tooth during the debonding operation extend in an occlusal-gingival direction and have a length less than the occlusal-gingival height of the bracket so that the instrument can be rocked to ensure that the pulling sections are in firm contact with the bracket during the time that the bracket is debonded from the tooth.

7 Claims, 2 Drawing Sheets

DEBONDING INSTRUMENT FOR ORTHODONTIC BRACKETS

BACKGROUND OF THE INVENTION

1. Field of the Invention

This invention relates to an instrument for debonding orthodontic brackets from teeth.

2. Description of the Related Art

A widely used tool for removing orthodontic brackets from teeth is described in U.S. Pat. No. 4,553,932, owned by the assignee of the present invention. The tool in U.S. Pat. No. 4,553,932 includes an L-shaped body with a handle and a pair of spaced apart abutments which straddle the bracket on occlusal and gingival sides to engage the tooth. The tool also includes a second class lever pivotally attached to the body, and the lever is connected to a single length of wire having a loop adapted to engage a single tie wing of the bracket. By moving the lever relative to the body while the abutments contact the tooth, the loop exerts a rotational-type pulling force to peel one side of the bracket base away from the tooth while the other side of the bracket base is at least initially still in contact with the tooth.

While the tool described in U.S. Pat. No. 4,553,932 has performed satisfactorily for brackets made of metallic materials, newer brackets made of brittle material such as ceramics including polycrystalline alumina may fracture when subjected to a rotational or peeling-type of debonding operation. In addition, the wings of ceramic brackets are much more susceptible to breakage while in tension during a debonding operation than wings of a comparable size of a metal bracket. For these reasons, the tool described in U.S. Pat. No. 4,553,932 has not been widely used in connection with ceramic brackets.

In the past, attempts have been made to remove ceramic brackets by a plier-like tool having a pair of opposed jaws with sharpened tips. In use, the tips are placed adjacent to the bonding adhesive between the base of the bracket and the tooth, and the tool is then squeezed to urge the tips together and pry and lift the bracket on both sides from the tooth. This type of debonding operation, however, may damage enamel on the tooth surface when the tips of the tool slide in wedging fashion across the tooth and beneath the bracket.

SUMMARY OF THE INVENTION

The present invention is directed toward an instrument for debonding an orthodontic bracket having occlusal and gingival wings from a tooth and comprises a body and a lever movably connected to the body. A pair of arms are connected to the lever and have pulling sections adapted to engage the bracket behind the occlusal and gingival wings and simultaneously exert a pulling force on the occlusal and gingival wings upon movement of the lever relative to the body. A pair of elongated reaction supports are connected to the body and extend in an occlusal-gingival direction contacting the tooth on the mesial and distal sides thereof when the pulling sections are in engagement with the bracket behind the occlusal and gingival wings.

As such, the pair of arms with the pulling sections are operable to lift the bracket from the tooth in a motion that is substantially perpendicularly away from the tooth surface without imposing a rotational force on the bracket that might otherwise cause a portion of the bracket to fracture. Moreover, the mesial-distal reaction supports enable the user to rock the body relative to the tooth while keeping the supports in contact with the tooth in order to enable both of the pulling sections to firmly grasp the bracket behind the wings even when such wings may not be the same height from the tooth surface.

DESCRIPTION OF THE PREFERRED EMBODIMENT

Figure 1:
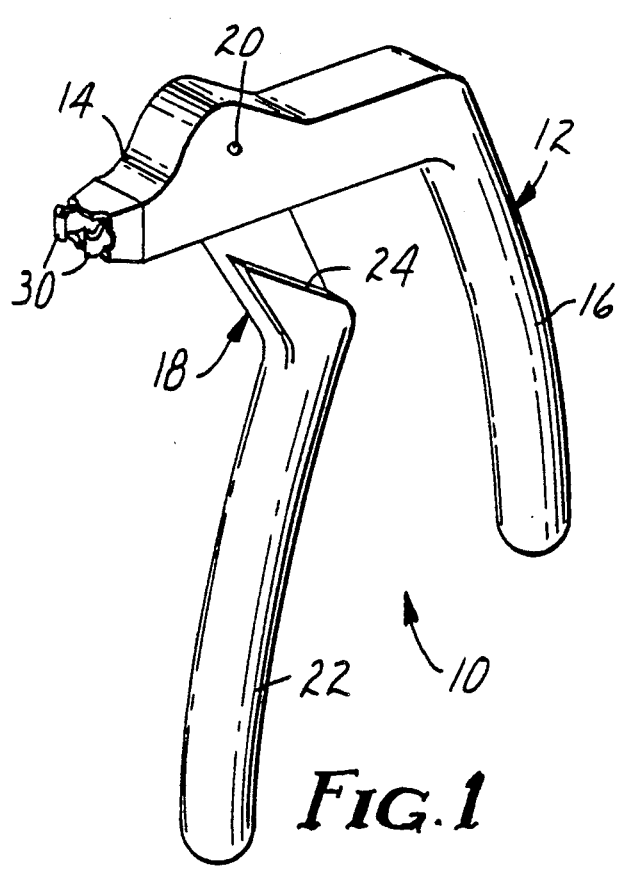
FIG. 1 is a perspective view of an instrument in accordance with the present invention.
Figure 2:
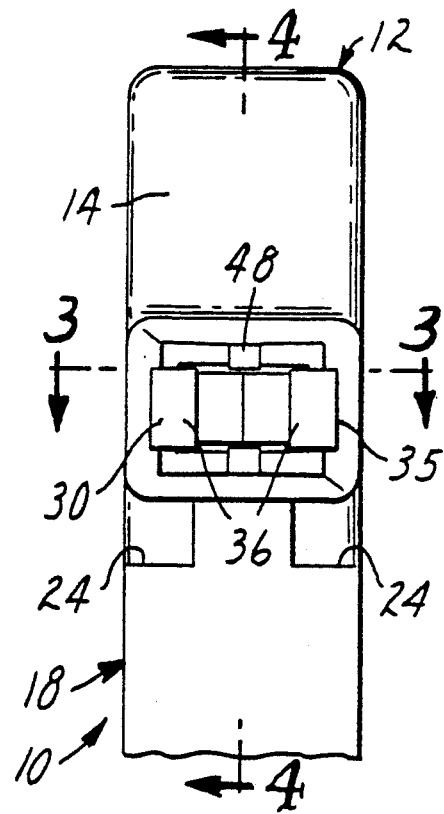
FIG. 2 is a fragmentary, enlarged, end elevational view of a head of the instrument shown in FIG. 1.
Figure 3:
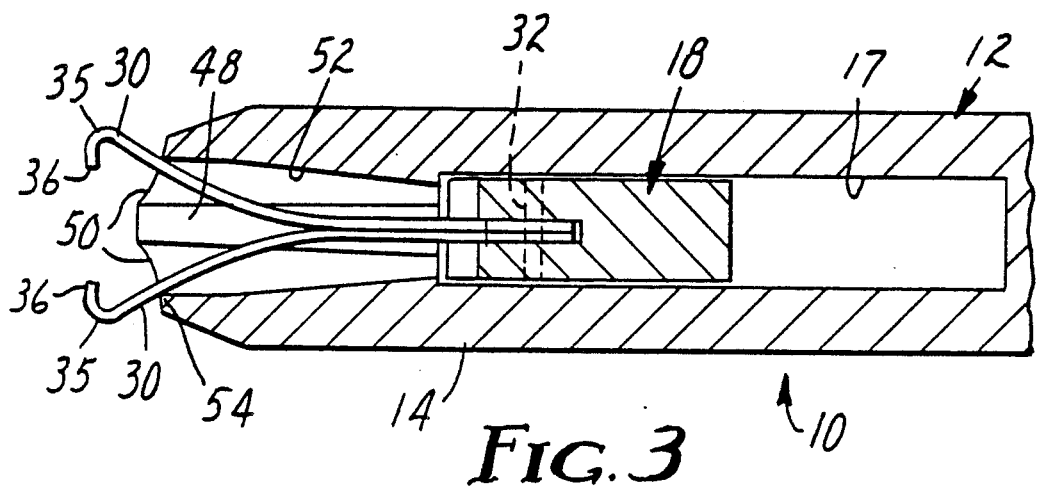
FIG. 3 is a fragmentary cross-sectional view of the head of the instrument taken along lines 3—3 of FIG. 2.

An instrument 10 for debonding orthodontic brackets from teeth is shown in FIGS. 1–7 and includes a main L-shaped body 12 that can best be appreciated by reference to FIG. 1. The body 12 includes a head portion 14 and a remote grip portion 16, and the head portion 14 includes a cavity 17 (FIGS. 3–4) which receives one end of a lever 18.

Figure 4:
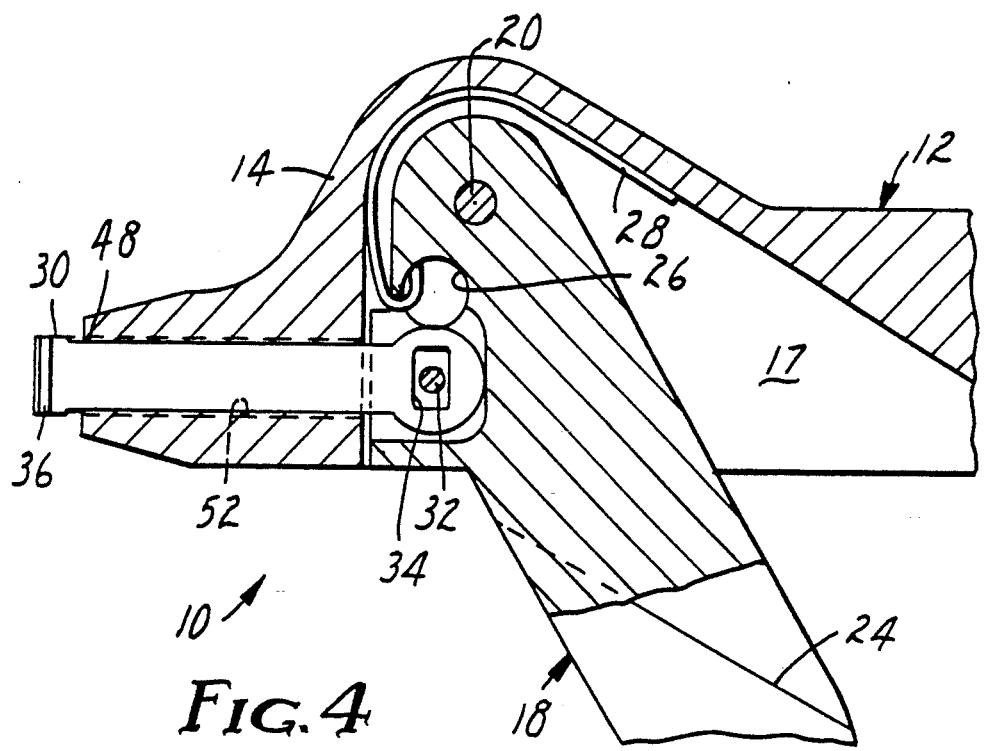
FIG. 4 is a fragmentary cross-sectional view of the head of the instrument taken along lines 4—4 of FIG. 2.

The lever 18 is pivotally connected to the body 12 by a pin 20. The lever 18 includes a handle portion 22, along with a pair of shoulders 24 (only one shown) which limit movement of the handle portion 22 toward the grip portion 16. As illustrated in FIG. 4, the lever 18 also has a recess 26 that receives one end of a flat spring 28 which tends to urge the lever 18 with the handle portion 22 away from the grip portion 16 to the position shown in FIGS. 1–5.

A pair of arms 30 formed from flat metal stock are coupled on one end by a pin 32 (FIGS. 3 and 4) to a portion of the lever 18 between the pivot pin 20 and the handle portion 22, thereby establishing a second class lever arrangement. The arms 30 are made with an enlarged, somewhat square aperture 34 that loosely receives the pin 32. The arms 30 are formed to have an inherent bias away from each other to the position shown in FIGS. 2, 3 and 5.

Figure 5:
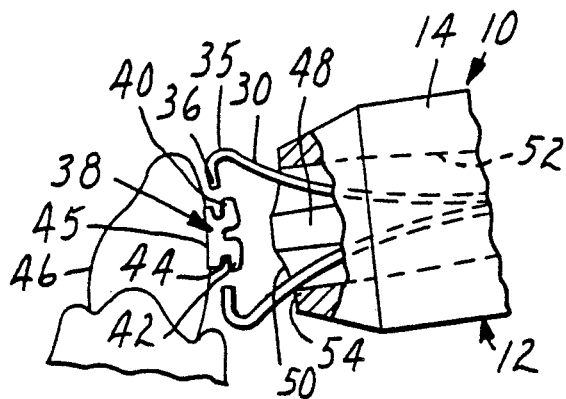
FIG. 5 is an enlarged, fragmentary top view of the head of the tool depicted in FIG. 1 showing a pair of arms with pulling sections about to engage an orthodontic bracket that is directly bonded to a tooth.
Figure 7:
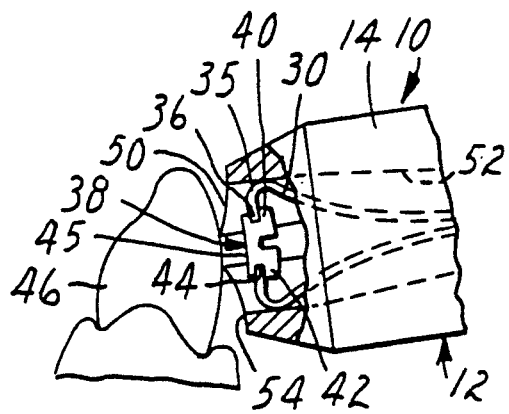
FIG. 7 is a view substantially similar to FIG. 6 except that the pulling sections have been moved away from the tooth to lift the bracket from the tooth while the reaction supports remain in contact with the tooth.
Figure 6:
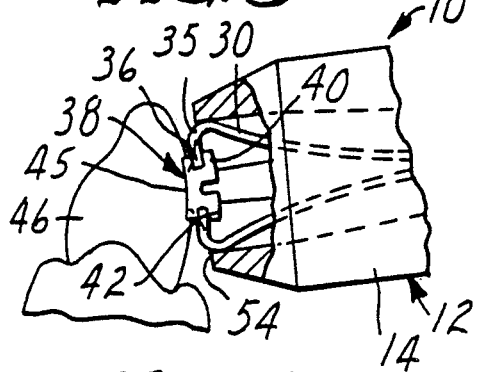
FIG. 6 is a view substantially similar to FIG. 5 except that the pulling sections have engaged the bracket while a pair of reaction supports (only one shown) straddle the bracket on mesial and distal sides.

The forward end of each of the arms 30 is somewhat L-shaped and includes a pulling section 35 with a flattened, elongated edge 36 having a length that is substantially equivalent to the mesial-distal width of ceramic brackets. A typical ceramic orthodontic bracket 38 is shown in FIGS. 5–7 and includes an occlusal wing 40 and a gingival wing 42, both of which extend across substantially the entire mesial-distal width of the bracket 38. A ligature groove 44 is located behind the wings 40, 42 and adjacent a base 45 of the bracket 38 which is directly bonded to a tooth 46 by a suitable adhesive.

A pair of elongated, projecting reaction supports 48 are fixedly connected to the body 12 on opposite sides of the edges 36 of the arms 30. Each of the supports 48 extends in a occlusal-gingival direction a short distance which is less than the occlusal-gingival height of the bracket 38 as can be appreciated by reference to FIGS. 5-7. The head portion 14 is cut away at 50 on each side of the supports 48 to ensure that only the supports 48 of the head portion 14 come in contact with the tooth 46.

In use, the instrument 10 is brought toward the tooth 46 until the edges 36 of the pulling sections 35 are directly adjacent the ligature groove 44 as shown in FIG. 5. (Advantageously, the thickness of the edges 36 is substantially the same dimension as the width of the groove 44.) Next, the instrument 10 is squeezed to move the handle portion 22 toward the grip portion 16, causing the lever 18 to swing around pivot pin 20 against the bias of the spring 28. The lever 18, in turn, moves the arms 30 rearwardly along a channel 52 formed in the head portion 14. The channel 52 terminates in a pair of corners or camming surfaces 54 along which the outer sides of the arms 30 slide, and the surfaces 54 move the pulling sections 35 toward each other to enable the edges 36 to firmly seat in the ligature groove 44 and grasp the bracket 38 behind the wings 40,42 in the manner indicated in FIG. 6.

The reaction supports 48 engage the tooth 46 once the edges 36 are in firm contact with the bracket 38. The user may rock the body 12 about an axis parallel to the pivot pin 20 while the supports 48 are in contact with the tooth 46 in order to ensure that the edges 36 are in firm, gripping contact with the ligature grooves 44. Such a procedure also increases the likelihood that the supports 48 are in flat edgewise contact with the tooth 46 so that patient discomfort may be minimized. The cut-away areas 50 of the head portion 14 help to avoid impingement of the head portion 14 with the tissues of the patient when reaction forces are applied to the tooth 46.

Once the arms 30 are in the position shown in FIG. 6 and the reaction supports 48 are in contact with the tooth, the outer corners of the L-shaped arms 30 are located within the channel 52 and rearwardly of the camming surfaces 54. As such, further movement of the handle portion 22 toward the grip portion 16 causes the arms 30 to move perpendicularly away from the tooth 46 without increasing the pressure of the pulling sections 35 toward each other or toward the ligature groove 44 in an occlusal-gingival direction. Continued movement of the handle portion 22 toward the grip portion 16 causes the bracket 38 to be lifted from the tooth 46 by both of the arms 30 simultaneously. As a consequence, rotational movement of the bracket 38 during debonding is substantially avoided and the likelihood of breakage of the wings 40,42 is reduced inasmuch as both wings 40,42 are gripped substantially along their entire extent.

I claim:

1. An instrument for debonding an orthodontic bracket having occlusal and gingival wings from a tooth comprising:

a body;

a lever movably connected to said body;

a pair of arms connected to said lever and each having a pulling section, said pulling sections adapted to engage the bracket behind both of the occlusal and the gingival wings and exert a pulling force on the occlusal and gingival wings simultaneously upon movement of said lever relative to said body; and a pair of reaction supports connected to said body and extending in an occlusal-gingival direction contacting the tooth along the mesial and distal sides of the bracket when both of said pulling sections are in engagement with the bracket behind the occlusal and gingival wings.

2. The instrument of claim 1, wherein said pulling sections extend at least substantially the entire width of the wings.

3. The instrument of claim 1, wherein said reaction supports are of a length less than the occlusal-gingival height of the bracket in order to permit rocking of the body as the pulling sections engage the bracket for permitting firm engagement with the bracket behind both of the wings.

4. The instrument of claim 1, wherein said body includes at least one camming surface engageable with at least one arm as said lever is moved relative to said body in order to move the pulling sections toward each other to engage the bracket.

5. The instrument of claim 4, wherein said body includes a channel and said arms extend through said channel, said at least one camming surface being located on one side of said channel.

6. The instrument of claim 1, wherein said body includes camming surfaces engageable with said arms and wherein said camming surfaces have a configuration adapted to initially move said arms toward each other as said lever is moved relative to said body to enable said pulling sections to engage the bracket and wherein said configuration enables said arms to move perpendicularly away from the tooth at substantially the same distance away from each other as said lever subsequently continues to be moved in order to lift the bracket from the tooth.

7. The instrument of claim 6, wherein said arms are normally biased away from each other.

* * * * *